United States Patent
Stierstorfer et al.

(10) Patent No.: US 7,056,018 B2
(45) Date of Patent: Jun. 6, 2006

(54) METHOD FOR DETERMINING CORRECTION COEFFICIENTS FOR DETECTOR CHANNELS FOR A COMPUTED TOMOGRAPH

(75) Inventors: Karl Stierstorfer, Erlangen (DE); Thomas Stoeger-Haselboeck, Vienna (AT)

(73) Assignee: Siemens Aktiengesellschaft, Munich (DE)

( * ) Notice: Subject to any disclaimer, the term of this patent is extended or adjusted under 35 U.S.C. 154(b) by 425 days.

(21) Appl. No.: 10/448,357

(22) Filed: May 30, 2003

(65) Prior Publication Data

US 2004/0022364 A1 Feb. 5, 2004

(30) Foreign Application Priority Data

May 31, 2002 (DE) .......................... 102 24 315

(51) Int. Cl.
*G01D 18/00* (2006.01)

(52) U.S. Cl. .................. 378/207; 378/18; 378/19
(58) Field of Classification Search .............. 378/4, 378/18, 19, 207; 250/252.1
See application file for complete search history.

(56) References Cited

U.S. PATENT DOCUMENTS

| 5,095,431 | A | * | 3/1992 | Feldman et al. | ............ 378/207 |
| 5,214,578 | A | * | 5/1993 | Cornuejols et al. | ......... 378/207 |
| 5,225,979 | A | * | 7/1993 | Feldman et al. | ............ 378/207 |

* cited by examiner

*Primary Examiner*—Edward J. Glick
*Assistant Examiner*—Courtney Thomas
(74) *Attorney, Agent, or Firm*—Harness, Dickey & Pierce, P.L.C.

(57) ABSTRACT

A method is for determining correction coefficients or parameters, in particular channel correction coefficients and/or spacing coefficients, for detector channels for a computed tomograph. In the method, a scan is carried out in order to obtain a sinogram of a phantom (11) which is formed with a smooth cross-sectional profile and is inserted into the computed tomograph in such a way that two or more different attenuation values are detected in a full scan of virtually all the detector channels (3). Attenuation profiles that are obtained from the sinogram are subjected to high-pass filtering for each projection of the scan, in order to obtain discrepancies of an ideal profile which is predetermined by the phantom (11). A model function is matched to the discrepancies that are obtained for each of the detector channels (3) as a function of the detected attenuation values, from which the coefficients or parameters are obtained. The method allows the channel correction coefficients to be determined easily, and the spacing coefficients also can be determined easily at the same time.

29 Claims, 4 Drawing Sheets

METHOD FOR DETERMINING CORRECTION COEFFICIENTS FOR DETECTOR CHANNELS FOR A COMPUTED TOMOGRAPH

The present application hereby claims priority under 35 U.S.C. §119 on German patent application number DE 10224315.8 filed May 31, 2002, the entire contents of which are hereby incorporated herein by reference.

FIELD OF THE INVENTION

The present invention generally relates to a method for determining correction coefficients or parameters. In particular, in relates to method for determining channel correction coefficients and/or spacing coefficients, for detector channels for a computed tomograph, by measurements using a phantom.

BACKGROUND OF THE INVENTION

A computed tomograph comprises, inter alia, an X-ray tube, X-ray detectors arranged in the form of rows or a matrix and which represent individual detector channels, and a table on which the patient is supported. The X-ray tube and the X-ray detectors are arranged on a gantry which rotates around the table on which the patient is supported, or around an examination axis running parallel to it, during the measurement. As an alternative to this, the X-ray detectors may also be arranged on a fixed detector ring around the table on which the patient is supported, with the X-ray tube being moved with the gantry.

The table on which the patient is supported can generally be moved relative to the gantry along the examination axis. The X-ray tube produces a focused beam which widens in the form of a fan in a slice plane at right angles to the examination axis. The boundary of this focused beam in the direction of the slice thickness is set by means of the size or the diameter of the focus on the target material of the X-ray tube and one or more shutters which are arranged in the beam path of the focused X-ray beam. During examinations in the slice plane, the focused X-ray beam passes through a slice of an object, for example a body slice of a patient who is supported on the table on which the patient is supported, and strikes the X-ray detectors which are opposite the X-ray tube. The angle at which the focused X-ray beam passes through the body slice of the patient and, if appropriate, the position of the table on which the patient is supported vary relative to the gantry continuously while images are being recorded by the computed tomograph.

The intensity of the X-rays in the focused X-ray beam which strike the X-ray detectors after passing through the patient is dependent on the attenuation of the X-rays as they pass through the patient. In this case, each of the X-ray detectors produces a voltage signal as a function of the intensity of the received X-ray radiation, which voltage signal corresponds to a measurement of the global transparency of the body for X-rays from the X-ray tube to the corresponding X-ray detector or detector channel. A set of voltage signals from the X-ray detectors, which correspond to attenuation data from which attenuation values are calculated, and which have been recorded for a specific position of the X-ray source relative to the patient is referred to as a projection. A set of projections which have been recorded at different positions of the gantry during rotation of the gantry around the patient is referred to as a scan. The computed tomograph records a large number of projections with the X-ray source in different positions relative to the body of the patient, in order to reconstruct an image which corresponds to a two-dimensional section image through the body of the patient, onto a three-dimensional image. The normal method for reconstruction of a section image from recorded attenuation data or from attenuation values derived from such data is referred to as the filtered back-projection method.

The reconstruction process is based on the fact that it is possible to calculate correct attenuation values for each detector channel k and for each projection angle of the gantry or each projection p. However, in practice, the detectors are never perfect. In fact, in addition to other faults, they have individual spectral nonlinearities, which may differ from channel to channel. Thus, the attenuation values $$x_k(d) = -\ln\left(\frac{I_k(d)}{I_{ok}}\right)$$

which are calculated from the signal from the individual detector elements or detector channels is a function of the thickness d of the material through which the radiation has passed, and which also depends on the respective detector channel k. $I_k(d)$ represents the remaining signal of the X-ray radiation as measured by the detector channel k after passing through the material or the body, and $I_{ok}$ represents the corresponding unattenuated signal. The dependency $x_k(d)$ measured using X-ray detectors is admittedly nonlinear in any case owing to the hardening of the beam as it passes through the material, but this nonlinearity can be taken into account jointly in the data evaluation by means of an appropriate beam hardening correction, jointly for all the channels. The remaining errors must be detected in a separate correction process. A correction process such as this, in particular for the described spectral nonlinearities, is necessary in order to avoid image artifacts in the form of rings in the images recorded with the computed tomograph.

In this case, it is known for these channel-specific spectral errors to be approximated by use of a polynomial, which is specific to each detector channel k, in the form:

$$\Delta x_k^{ccr} = \sum_{n=1}^{N} a_{k,n} \cdot x_k^n$$

where the degree of polynomial N is generally not greater than 2. The data measured with each detector element or detector channel is in this case converted to logarithmic form in the known manner described above, in order to obtain an attenuation value $x_k$. This attenuation value is finally corrected by use of the correction value $\Delta x_k^{ccr}$ which is determined specifically for each channel, before the filtered back-projection process is carried out using the attenuation values.

The major technical problem with this type of correction is to determine the polynomial coefficients $a_{k,n}$, which are also referred to as channel correction coefficients in the following text. At the moment, measurements are carried out on bar phantoms of different thickness, without the gantry being rotated, in order to determine the polynomial coefficients using the computed tomograph. These measurements result in two or more different attenuation values for each detector channel. From these, if the attenuation of the respectively used phantoms is known, it is possible to determine a discrepancy from the correct value, and thus the correction coefficients. However, measurement by using these bar phantoms is tedious. Furthermore, the bar phantoms are relatively bulky and must be delivered with each computed tomography system and must be stored at the point where they are used. The measurement must also be carried out on a non-rotating system, so that the system state when determining the correction coefficients does not correspond to the state in which it is used for an actual measurement. In particular, the temperature conditions when the system is in the stationary state may differ considerably from the temperature conditions in the rotating state.

A further type of fault which is caused by the detector elements in the computed tomograph is so-called spacing errors, which are caused by the detector layout not being geometrically equidistant. To a first approximation, these spacing errors can be approximated by the following formula:

$$\Delta x_k^{sp} = c_k \cdot \frac{\partial x_k}{\partial k}.$$

In addition, the spacing coefficients $c_k$ must be determined in order to use this correction for the attenuation values $x_k$ which are derived from the measurements. These spacing coefficients $c_k$ have until now been determined by a scan of a cylindrical phantom made of plexiglass with a relatively small diameter of only 40 mm, which is positioned eccentrically within the examination area of the computed tomograph. The sinogram which is obtained in this way is first of all used to determine the position of the phantom within the computed tomograph. This position is then compared with the data obtained for each detector channel, and the correction coefficient is derived from the distance between the respective maxima. Both the positioning of the phantom and the data evaluation are, however, relatively complex.

SUMMARY OF THE INVENTION

Against the background of this prior art, an object of an embodiment of the present invention is to specify a method for determining correction coefficients, in particular channel correction coefficients and/or spacing coefficients, for detector channels for a computed tomograph, which allows determination in a simple manner.

In at least one embodiment, a method for determining correction coefficients, in particular channel correction coefficients and/or spacing coefficients, for detector channels for a computed tomography includes steps wherein: a phantom with a smooth cross-sectional profile is inserted into the examination area of the computed tomograph in such a way that two or more different attenuation values are in each case detected during a full scan, that is to say during a measurement with a full revolution of the gantry, by virtually all the detector channels. After the insertion of the phantom, at least one scan is carried out in order to obtain a sinogram of the phantom. Attenuation profiles which are obtained from the sinogram for each projection of the scan are subjected to high-pass filtering, in order to obtain discrepancies from an ideal profile which is predetermined by the shape of the phantom.

A model function is then matched separately for each detector channel to the discrepancies that are obtained for the respective detector channel, as a function of the detector attenuation values, from which the correction coefficients or parameters are obtained.

Only a single phantom is therefore used for the method of an embodiment of the present application. This makes use of the fact that each detector channel measures not only a single attenuation value but a large number of attenuation values by virtue of the different projections of a scan, if the phantom is arranged in a suitable manner, and these attenuation values can be used to derive the correction coefficients if the geometric shape of the phantom is known. The use of a phantom with a smooth cross-sectional profile, that is to say without any edges or surface structure discontinuities, together with the subsequent high-pass filtering makes it possible to obtain the channel-specific discrepancy from the ideal profile as predetermined by the shape of the phantom, since this discrepancy varies to a major extent from channel to channel.

The data contained in the sinogram may be used with the method of an embodiment of the application in order to determine the channel correction coefficients or parameters and/or in order to determine the spacing coefficients. These discrepancies can also be used to determine a correction for the air calibration tables, that is to say a constant $\Delta x_k^{air} = d_k$. The air calibration table takes account of the different gain in the detector channels.

There is no need for any more different phantoms if the channel correction coefficients or parameters and the spacing coefficients are determined jointly. In fact, a single measurement is sufficient, that is to say a single scan, when using the present phantom with a smooth cross-sectional profile. There is no longer any need to use different, bulky bar phantoms. The calibration measurements are carried out on the rotating system, so that the conditions for an actual measurement are satisfied. Furthermore, there is also no longer any need for critical positioning of the phantom or for complex evaluation of the data in order to determine the spacing coefficients.

With a method of an embodiment of the present application, a cylindrical phantom is preferably used, for example a phantom with a diameter between 15 and 30 cm, which is arranged eccentrically within the examination area with can be covered by the detector channels. This eccentric arrangement establishes that all of the detector channels, or at least the majority of the detector channels, each see and measure different attenuation values during one revolution. The application of the high-pass filtering to the signals or attenuation values that are obtained with each projection and which represent an attenuation profile, as a function of the channel, results in discrepancies from the actual smooth profile of the phantom (which is referred to as the ideal profile in the present patent application) being filtered out, with these discrepancies resulting from noise, spacing errors and channel-specific spectral nonlinearities.

The high-pass filtering may, of course, be carried out in different ways, as long as this filtering allows the channel-specific discrepancies from the ideal profile to be obtained, with this filtering generally including a mathematical operation for obtaining fluctuation amplitudes of attenuation values which fluctuate severely between the detector channels. One example for the high-pass filtering is the subtraction of a smoothed profile from the measurement or attenuation profile that is obtained. The smoothed profile can be obtained by convolution of the measured profile with suitable filter cores, for example by using one, or possible more than one, square-wave filter, Gaussian filter, Savitsky-Golay filter, etc. Furthermore, the smoothed profile can be achieved by means of polynomial approximation, or a fit by means of the measured profile. A further possibility is to match a theoretically calculated smooth attenuation profile to the measured profile by means of a fit. The discrepancies to be determined are obtained by subtracting the respectively smoothed profile from the measured profile, and these are then subjected to further processing. A further option for high-pass filtering is convolution of the data of the respective measured profile using a specific high-pass filter, similar to the convolution core that is used for the reconstruction of the CT image data. In this situation, it may also be necessary to subtract a smoothed profile subsequently.

The row-by-row application of the high-pass filter to the data from the sinogram, with the expression row-by-row in this context meaning application in the channel direction of the sinogram, results in the channel-specific discrepancies from the respective ideal value for different attenuations. The relationship between the discrepancies and the attenuation can now be modeled for each channel by adaptation of a model function, from which the desired channel correction coefficients or spacing coefficients are then obtained. A polynomial is preferably used for determining the channel correction coefficients, as has already been described in the introductory part of the description. This also applies to determining the spacing coefficients. If both coefficients are intended to be determined at the same time, then the model function is additively composed of the two said polynomials. The matching process itself can be carried out using known methods, for example a least squares fit by minimizing the sum of the errors.

Furthermore, an air calibration can be carried out at the same time that the spacing coefficients and/or the channel correction coefficients are determined, by adding the channel-dependent constant $d_k$ to the respective model function, as a parameter to be determined for the air calibration.

The simple procedure in the method of an embodiment of the application allows this to be used with a single phantom which, for example, may be in the form of a water phantom.

The cross-sectional shape of this phantom is preferably chosen to be a geometric shape whose attenuation profile can be represented by a function that can be described mathematically. In this way, the high-pass filtering can be carried out very easily and accurately by subtraction of the matched predetermined function.

BRIEF DESCRIPTION OF THE DRAWINGS

The present invention will be explained once again briefly in the following text with reference to an exemplary embodiment and in conjunction with the drawings, in which.

DETAILED DESCRIPTION OF THE PREFERRED EMBODIMENTS

Figure 1:
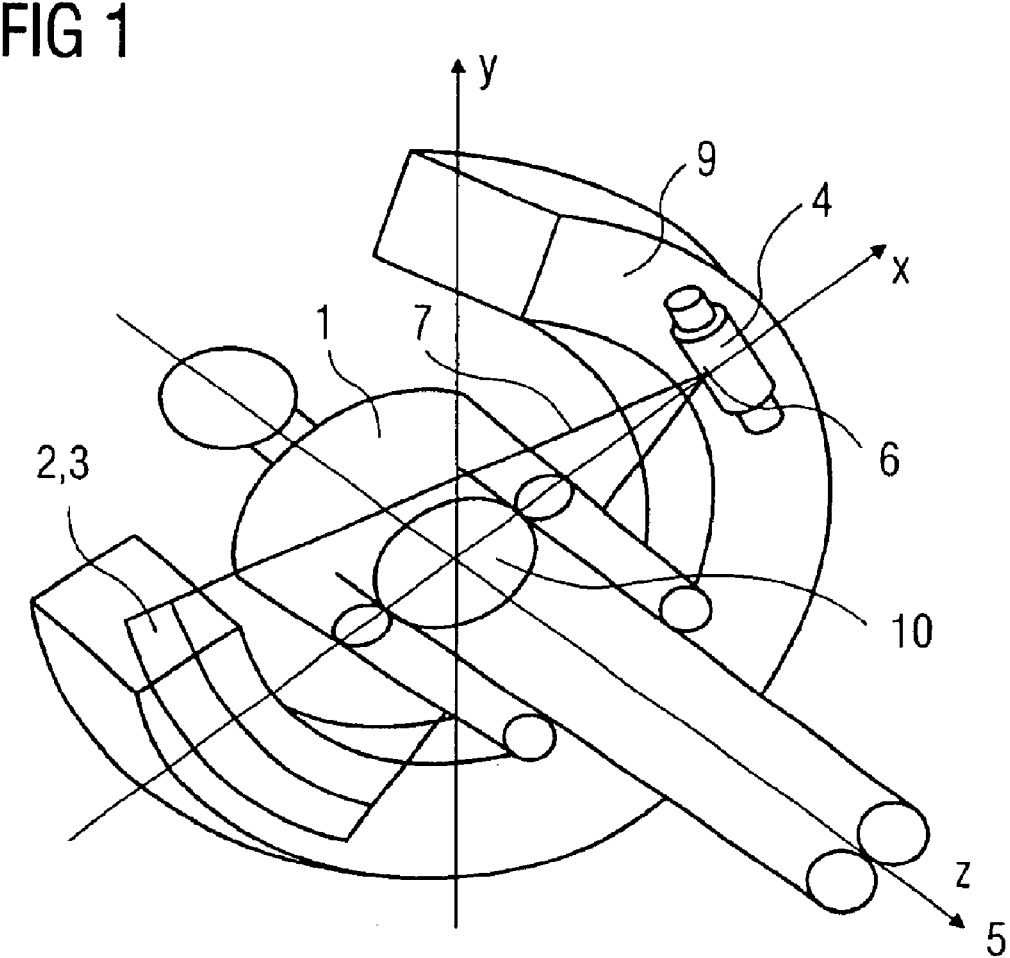
FIG. 1 shows a schematic view of part of a computed tomograph for obtaining section images of a body slice of a patient.

FIG. 1 shows a schematic view of a part of a computed tomograph, illustrating the geometric relationships for measurement data recording. The computed tomograph has an X-ray source in the form of an X-ray tube 4, which emits a fan-shaped focused X-ray beam 7 in the direction of a detector bank with a row 2 of detector elements 3. Both the X-ray tube 4 and the detector elements 3 are arranged on a gantry 9, which can rotate continuously around a patient 1. The patient 1 lies on a table which supports the patient, extends into the gantry 9, but is not shown in FIG. 1. The gantry 9 rotates in an x-y plane in a Cartesian coordinate system x-y-z as indicated in FIG. 1. The table which supports the patient can move along the z-axis, which corresponds to the slice thickness direction 5 of the respective slices of the patient 1 to be displayed. The figure also shows the slice 10 through which the focused X-ray beam 7 passes, and which is intended to be used to produce a slice image.

Figure 2:
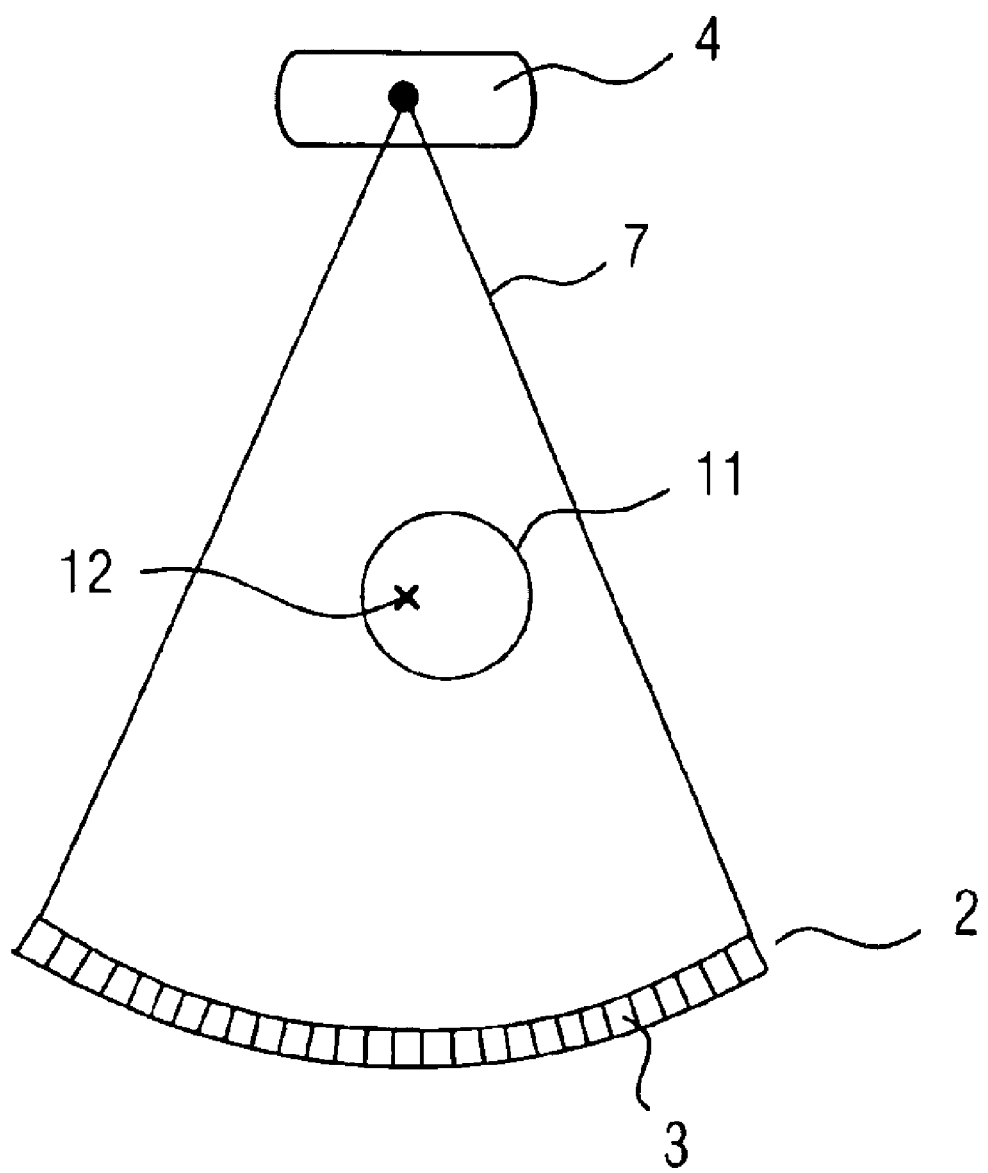
FIG. 2 shows a highly simplified illustration to show the position of a phantom for carrying out the present method.

FIG. 2 shows a different view of parts of the computed tomograph from FIG. 1, in which a cylindrical phantom 11 is inserted, eccentrically with respect to the rotation axis 12, instead of a patient, so that, with the exception of the outermost detector elements in the detector row 2, all the detector elements 3 detect a large number of different attenuation values of the phantom 11 during one revolution of the gantry 9.

Figure 3:
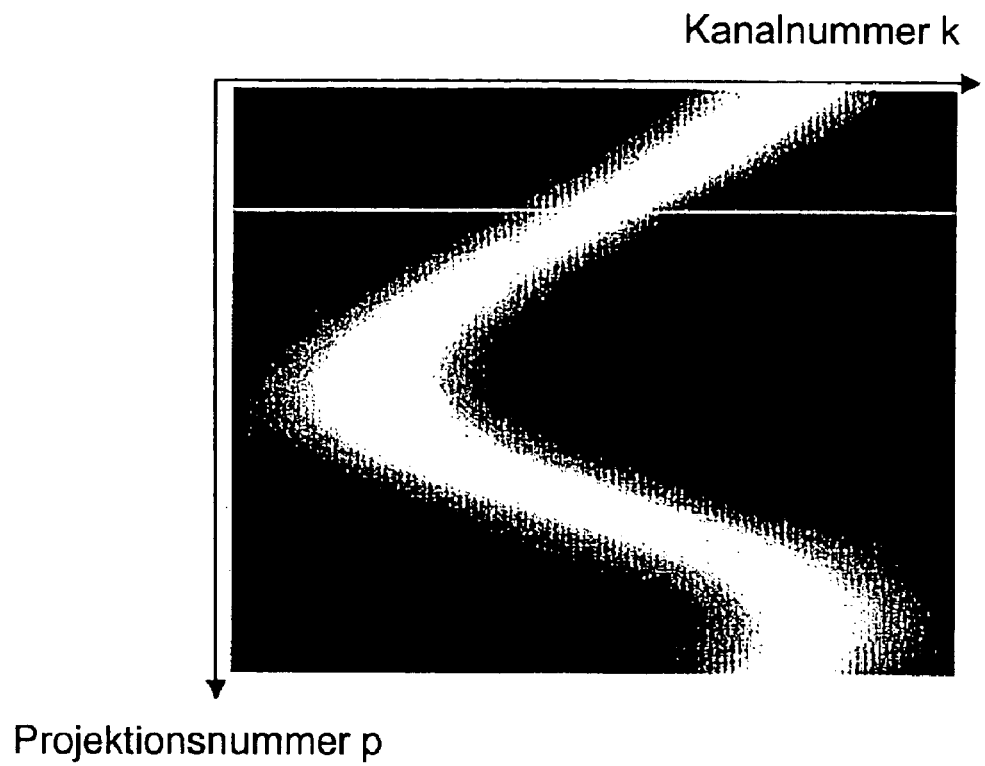
FIG. 3 shows a sinogram measured using such an arrangement.
Figure 4:
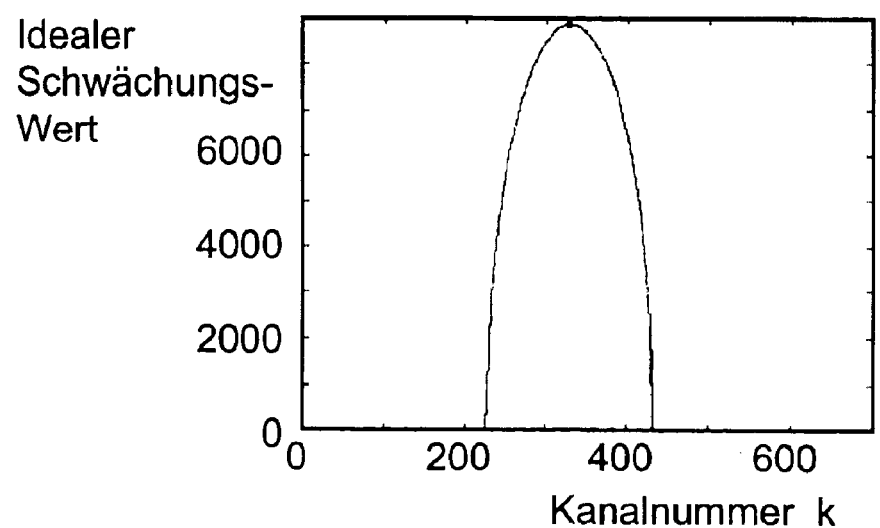
FIG. 4 shows an ideal attenuation profile, derived from the sinogram shown in FIG. 3, along the line illustrated in FIG. 3.

FIG. 3 shows an example of a sinogram, recorded in one scan, of a phantom such as this. The figure shows very well that, with the exception of the outermost channels, each detector channel measures a large number of attenuations by the phantom 11 during the scan. Related to this, FIG. 4 shows an ideal profile as is obtained from the phantom 11 in the projection indicated by a line in the sinogram in FIG. 3 when none of the detectors are faulty. In this case, as in the other projections of the present smooth phantom 11 as well, the attenuation profile has a profile which is likewise smooth.

Figure 5:
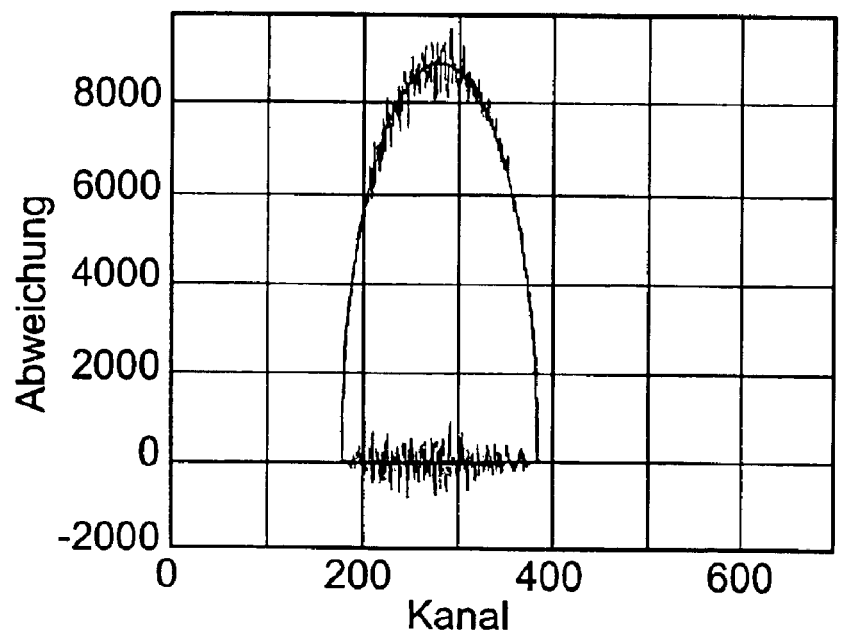
FIG. 5 shows an actual measured profile obtained from the sinogram, along the line illustrated in FIG. 3, as well as the data obtained from this by high-pass filtering.

However, the actually measured profile of the attenuation profile of a phantom such as this has a different appearance, due to the channel-specific detector error and the spacing errors, as can be seen from FIG. 5, which shows the measured profile actually obtained along the line in FIG. 3. The discrepancies from the smoothly plotted ideal profile can be seen clearly in the illustration in FIG. 5.

After obtaining the sinogram, the individual rows in the sinogram are filtered by using a suitable high-pass filter so as to obtain the discrepancies. The discrepancies are thus filtered out of the sinogram. In the present example, the filtering is carried out by subtraction of the smoothed profile (ideal profile), as can be seen in FIG. 5, from the respectively measured profile. The smoothed profile can be obtained by applying a suitable smoothing function to the measured profile. Other options have already been explained in the description above. After subtraction of the smoothed profile from the measured profile, an error or discrepancy profile is obtained, as can be seen from the lower part of the diagram in FIG. 5. The high-pass filtering thus produces the discrepancy $\Delta x_{kp}$ for each measurement value $x_{kp}$, when k is the channel number and p is the projection number of the scan or sinogram.

In the following text, the correction coefficients $a_{k,n}$, $c_k$ and $d_k$ for the channel correction, the spacing correction and the for the correction of the air calibration tables are determined as follows from the discrepancies obtained in the described manner for each channel k:

The $a_{k,n}$, $c_k$ and $d_k$ are determined which reduce, and preferably minimize, the error sum $$F = \sum_p \left( \Delta x_{kp} - \sum_{n=1}^{N} a_{k,n} x_{kp}^n - c_k \cdot \frac{\partial x_{kp}}{\partial k} - d_k \right)^2.$$

In this case, the model functions mentioned in the introduction to the description are used for the channel correction and for the spacing correction. The correction for the air calibration table corresponds to the function $\Delta x_k^{air} = d_k$.

In this procedure, $x_{kp}$ may be the measured value of the corresponding channel k for the corresponding projection p. However, if the high-pass filter has been implemented in the form of smoothing of the measured profile, the value obtained by smoothing for this channel may also be used for this value. If $x_{kp}$ is the actual measurement value, the derivative in the above formula for the error sum must be approximated by subtraction, for example by $$\frac{\partial x_{kp}}{\partial k} \approx \frac{1}{2}(x_{k+1,p} - x_{k-1,p}).$$

The same formula can be used if $x_{kp}$ is obtained by low-pass filtering. If the smoothing has been achieved by means of a fit to the measurement curve or measured profile, the derivative can also be obtained by analytical differentiation of the fitted function.

The channel-specific spectral nonlinearities can be modeled not only by a model function in the form of a polynomial but also by any other desired functional relationship $\Delta x_k^{ccr} = f_a(x_k)$, where a represents the vector of the model or correction parameters. The parameters a are then determined together with the above parameters c and d by minimizing the analogous error sum.

The optimization process may, of course, also be carried out by adapting just the model function of only one of the correction coefficients, for example only for the spacing coefficients or only for the channel correction coefficients. The corresponding other errors in the detector channels should then be calculated out, before this matching process, in a preprocessing step.

Figure 6:
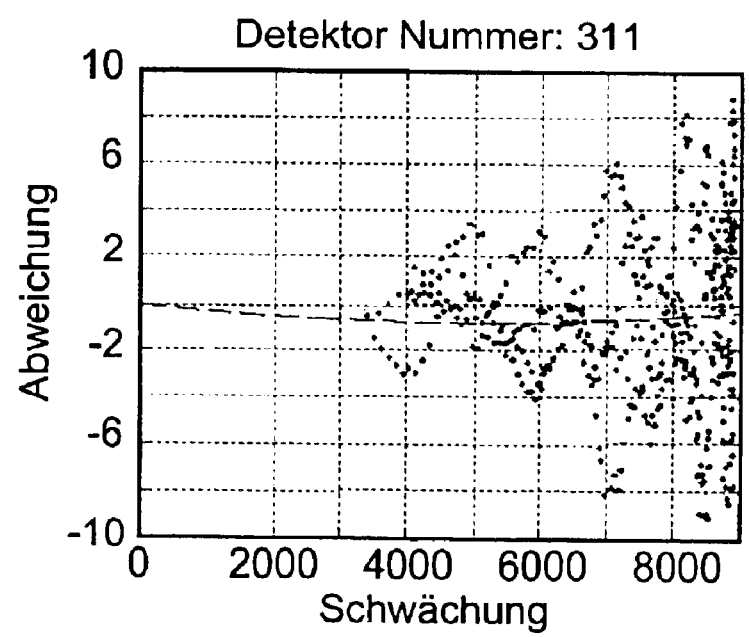
FIG. 6 shows an example of the discrepancies obtained from the sinogram, as a function of the attenuation for a single detector channel, as well as the profile of a model function matched to this.

By way of example, FIG. 6 shows a matched model function for determining the channel correction coefficients. This figure shows the discrepancies Δx obtained from the sinogram in FIG. 3 for one channel by high-pass filtering, as a function of the attenuation. The greatest scatter in these discrepancies which can be seen for relatively high attenuation values is caused by the increased quantum noise in the X-ray detector. The matched model function is represented by the dashed line. The coefficients $a_n$ for this channel can be determined from the matching of this model function to the determined discrepancies Δx.

In addition to the individual or joint determination of the correction coefficients for the spectral nonlinearities and the spacing errors and, if appropriate, the errors in the air calibration table, the individual coefficients can also be determined successively in a number of steps. It is thus possible, for example, to determine the channel correction coefficients first of all, after which the data is corrected using these coefficients, the spacing coefficients are then determined and, after appropriate correction to the data, these coefficients are used to determine the errors in the air calibration table.

The correction coefficients are generally determined before delivery of a computed tomograph as well as at regular servicing intervals or after repairs. The attenuation values measured during correct use of the computed tomograph are then in each case corrected automatically using the determined correction coefficients and the associated model functions or polynomials.

The present method may, of course, also be used for more row or area detectors, in which case the channels for each detector row must then be evaluated individually.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for determining at least one of correction coefficients and parameters for detector channels for a computed tomograph, comprising:

inserting a phantom with a smooth cross-sectional profile into the computed tomograph in such a way that at least two different attenuation values are detected in a scan, the phantom including a plurality of projections of virtually all the detector channels;

carrying out at least one scan in order to obtain a sinogram of the phantom;

subjecting attenuation profiles, obtained from the sinogram for each projection of the scan, to high-pass filtering in order to obtain discrepancies from an ideal profile which is predetermined by the phantom; and matching a model function, for each detector channel, to the discrepancies which are obtained for the detector channel, as a function of the detected attenuation values, from which the at least one of correction coefficients and parameters are obtained.

2. The method as claimed in claim 1, wherein a cylindrical phantom with a diameter in the range between 15 and 30 cm is used.

3. The method as claimed in claim 1, wherein the high-pass filtering is carried out by smoothing the attenuation profile that is in each case obtained from the sinogram, in order to obtain the ideal profile, and wherein the ideal profile is subtracted from the attenuation profile that is obtained from the sinogram.

4. The method as claimed in claim 1, wherein the high-pass filtering is carried out by way of a curve fit for the attenuation profile which is in each case obtained from the sinogram, in order to obtain the ideal profile, and wherein the ideal profile is subtracted from the attenuation profile that is obtained from the sinogram.

5. The method as claimed in claim 1, wherein the high-pass filtering is carried out by way of a curve fit for the attenuation profile which is in each case obtained from the sinogram, with a theoretically calculated attenuation profile in order to obtain the ideal profile, and wherein the ideal profile is subtracted from the attenuation profile that is obtained from the sinogram.

6. The method as claimed in claim 1, wherein the high-pass filtering is carried out by convolution of the attenuation profile that is in each case obtained from the sinogram, with a suitable function in order to obtain the ideal profile.

7. The method as claimed in claim 1, wherein a water phantom is used.

8. The method as claimed in claim 1, wherein a cylindrical phantom is used and is positioned eccentrically in the computed tomograph.

9. The method as claimed in claim 8, wherein the high-pass filtering is carried out by smoothing the attenuation profile that is in each case obtained from the sinogram, in order to obtain the ideal profile, and wherein the ideal profile is subtracted from the attenuation profile that is obtained from the sinogram.

10. The method as claimed in claim 8, wherein the high-pass filtering is carried out by way of a curve fit for the attenuation profile which is in each case obtained from the sinogram, in order to obtain the ideal profile, and wherein the ideal profile is subtracted from the attenuation profile that is obtained from the sinogram.

11. The method as claimed in claim 8, wherein the high-pass filtering is carried out by way of a curve fit for the attenuation profile which is in each case obtained from the sinogram, with a theoretically calculated attenuation profile in order to obtain the ideal profile, and wherein the ideal profile is subtracted from the attenuation profile that is obtained from the sinogram.

12. The method as claimed in claim 8, wherein the high-pass filtering is carried out by convolution of the attenuation profile that is in each case obtained from the sinogram, with a suitable function in order to obtain the ideal profile.

13. The method as claimed in claim 8, wherein a water phantom is used.

14. The method as claimed in claim 1, wherein the model function is adapted by minimizing an error sum over the projections.

15. The method as claimed in claim 14, wherein the error sum $$F = \sum_p (\Delta x_{kp} - f_a(x_{kp}))^2$$

is minimized using a model function $f_a(x_k)$ in order to determine channel correction parameters as the at least one of correction coefficients and parameters.

16. The method as claimed in claim 15, wherein, at the same time that at least one of the correction coefficients and parameters are determined, coefficients $d_k$ are determined for correction of an air calibration table.

17. The method as claimed in claim 14, wherein the error sum $$F = \sum_p \left(\Delta x_{kp} - \sum_{n=1}^{N} a_{k,n} x_{kp}^n\right)^2$$

is minimized using a model function $$\sum_{n=1}^{N} a_{k,n} \cdot x_k^n$$

in order to determine channel correction coefficients as the at least one of correction coefficients and parameters.

18. The method as claimed in claim 17, wherein, at the same time that at least one of the correction coefficients and parameters are determined, coefficients $d_k$ are determined for correction of an air calibration table.

19. The method as claimed in claim 14, wherein the error sum $$F = \sum_p \left(\Delta x_{kp} - c_k \cdot \frac{\partial x_{kp}}{\partial k}\right)^2$$

is minimized using a model function $$c_k \cdot \frac{\partial x_k}{\partial k}$$

in order to determine spacing coefficients as the at least one of correction coefficients and parameters.

20. The method as claimed in claim 19, wherein, at the same time that at least one of the correction coefficients and parameters are determined, coefficients $d_k$ are determined for correction of an air calibration table.

21. The method as claimed in claim 14, wherein the error sum $$F = \sum_p \left(\Delta x_{kp} - \sum_{n=1}^{N} a_{k,n} x_{kp}^n - c_k \cdot \frac{\partial x_{kp}}{\partial k}\right)^2$$

is minimized using a model function $$\sum_{n=1}^{N} a_{k,n} \cdot x_k^n + c_k \cdot \frac{\partial x_k}{\partial k}$$

in order to determine spacing coefficients and channel correction coefficients as the at least one of correction coefficients and parameters.

22. The method as claimed in claim 21, wherein, at the same time that at least one of the correction coefficients and parameters are determined, coefficients $d_k$ are determined for correction of an air calibration table.

23. The method as claimed in claim 14, wherein, at the same time that at least one of the at least one of correction coefficients and parameters are determined, coefficients $d_k$ are determined for correction of an air calibration table.

24. The method as claimed in claim 14, wherein the error sum $$F = \sum_p (\Delta x_{kp} - f_a(x_{kp}))^2$$

is reduced using a model function $f_a(x_k)$ in order to determine channel correction parameters as the at least one of correction coefficients and parameters.

25. The method as claimed in claim 14, wherein the error sum $$F = \sum_p \left(\Delta x_{kp} - \sum_{n=1}^{N} a_{k,n} x_{kp}^n\right)^2$$

is reduced using a model function $$\sum_{n=1}^{N} a_{k,n} \cdot x_k^n$$

in order to determine channel correction coefficients as the at least one of correction coefficients and parameters.

26. The method as claimed in claim 14, wherein the error sum $$F = \sum_p \left( \Delta x_{kp} - c_k \cdot \frac{\partial x_{kp}}{\partial k} \right)^2$$

is reduced using a model function $$c_k \cdot \frac{\partial x_{kp}}{\partial k}$$

in order to determine spacing coefficients as the at least one of correction coefficients and parameters.

27. The method as claimed in claim 14, wherein the error sum $$F = \sum_p \left( \Delta x_{kp} - \sum_{n=1}^{N} a_{k,n} x_{kp}^n - c_k \cdot \frac{\partial x_{kp}}{\partial k} \right)^2$$

is reduced using a model function $$\sum_{n=1}^{N} a_{k,n} \cdot x_k^n - c_k \cdot \frac{\partial x_k}{\partial k}$$

in order to determine spacing coefficients and channel correction coefficients as the at least one of correction coefficients and parameters.

28. A method for determining at least one of correction coefficients and parameters for detector channels for a computed tomograph, comprising:
   inserting a phantom into the computed tomograph such that at least two different attenuation values are detected in a scan, the phantom including a plurality of projections of a plurality of the detector channels;
   carrying out at least one scan to obtain a sinogram of the phantom;
   subjecting attenuation profiles, obtained from the sinogram for each projection of the at least one scan, to high-pass filtering to obtain discrepancies from a profile which is predetermined by the phantom; and
   determining the at least one of correction coefficients and parameters by matching a model function, for each detector channel, to the discrepancies obtained for the detector channel.

29. The method as claimed in claim 28, wherein a cylindrical phantom is used and is positioned eccentrically in the computed tomograph.

* * * * *